United States Patent [19]

Bader et al.

[11] 4,237,275
[45] Dec. 2, 1980

[54] PROCESS FOR PRODUCING HYDRAZONE DERIVATIVES OF PYRIDINALDEHYDES

[75] Inventors: Rolf Bader, Riehen, Switzerland; Dieter Reinehr, Kandern, Fed. Rep. of Germany

[73] Assignee: Ciba-Geigy Corporation, Ardsley, N.Y.

[21] Appl. No.: 42,828

[22] Filed: May 29, 1979

[30] Foreign Application Priority Data

Jun. 8, 1978 [CH] Switzerland .................. 6287/78

[51] Int. Cl.³ .......................................... C07D 213/53
[52] U.S. Cl. ................................. 542/417; 546/314; 546/315
[58] Field of Search ................ 542/417; 546/314

[56] References Cited

U.S. PATENT DOCUMENTS

| | | | |
|---|---|---|---|
| 2,749,351 | 6/1956 | Mathes et al. | 546/314 |
| 3,008,963 | 11/1961 | Mathes et al. | 546/340 |
| 3,160,633 | 12/1964 | Cislak | 546/286 |
| 3,274,206 | 9/1966 | Wilbert et al. | 546/314 |
| 3,573,287 | 3/1971 | Schorr et al. | 542/417 |

*Primary Examiner*—Alan L. Rotman
*Assistant Examiner*—Natalia Harkaway
*Attorney, Agent, or Firm*—Prabodh I. Almaula

[57] ABSTRACT

An improved process for producing pyridinaldehydes and hydrazone derivatives thereof, for example, pyridinaldehyde-phenylhydrazones, is described. This comprises reacting a aminomethylpyridine with an aldehyde or a ketone to give a compound of the formula

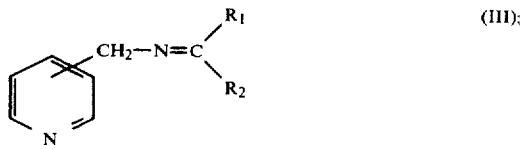

isomerizing the compound (III), in the presence of suitable catalysts, to a compound of the formula

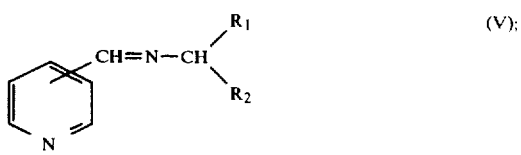

and converting the compound (V), in the presence of an acid and optionally in the presence of a hydrazine, into a pyridinaldehyde or a pyridinaldehyde-hydrazone. It is possible to produce by the process according to the invention pyridinaldehydes and pyridinaldehyde-hydrazones in a simple manner, under mild ecologically favorable conditions and in good to very good yields.

12 Claims, No Drawings

PROCESS FOR PRODUCING HYDRAZONE DERIVATIVES OF PYRIDINALDEHYDES

The present invention relates to a new process for producing pyridinaldehydes and derivatives thereof.

Numerous process for producing pyridinaldehydes are known from the literature. The nearest comparable process which may be mentioned is the so-called Sommelet reaction, by means of which 3-pyridinaldehyde can be produced, in a yield of 57% of theory, by reaction of 3-aminomethylpyridine with hexamethylenetetramine at a pH value of between 3 and 6.5. 2- and 4-Pyridinaldehyde cannot however be produced by this method [see J. Chem. Soc., 1953, 1740–41].

Pyridinaldehydes can be produced also by catalytic hydrogenation of cyanopyridines (see for example German Pat. No. 1,088,958, DDR Pat. No. 43,044, and U.S. Pat. Nos. 3,274,206 and 3,160,633. These hydrogenation processes are unsatisfactory in that they require special measures for checking the hydrogen absorption and hence for reducing undesirable secondary reactions, and/or they require large amounts of expensive catalysts, which, moreover, are partially soluble in the reaction medium and the processing of which is complicated. Furthermore, the reactions have to be performed under rigorous reaction conditions, such as in a strongly acid medium, under high pressure or at high temperatures. The yields are in some cases also unsatisfactory.

The production of pyridinaldehydes by means of catalytic oxidation of methylpyridines in the gaseous phase at temperatures of between about 370° and 420° C. likewise requires rigorous reaction conditions. This process is complicated both with regard to the necessary apparatus and with regard to the reaction conditions (U.S. Pat. No. 2,749,351).

It is possible by using a further process (U.S. Pat. No. 3,008,963) to produce pyridinaldehydes also by heating the appropriate pyridine-N-oxide-carbinols to temperatures between about 250° and 450° C. The producing of the pyridine N-oxide-carbinols with their conversion into pyridinaldehydes is however not without danger, because explosions can occur on heating the pyridine-N-oxide-carbinols. This process moreover produces satisfactory yields only in the case of 2-pyridinaldehyde.

The present invention relates therefore to a new process by which it is possible to produce pyridinaldehydes and derivatives thereof in a simple manner, under mild, ecologically favourable reaction conditions, in good to very good yields, and also on a large commercial scale.

Compounds of the formula I

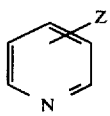

(I)

wherein
Z is —CHO or

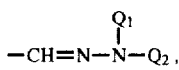

$Q_1$ is hydrogen or alkyl having 1–4 C atoms, and $Q_2$ is phenyl which can be substituted by halogen atoms, alkyl or alkoxy groups each having 1–4 C atoms, or is naphthyl, can be obtained by the process of the invention by reacting an aminomethylpyridine with a compound of the formula II

(II)

wherein
$R_1$ is hydrogen or alkyl having 1–8 C atoms,
$R_2$ is alkyl having 1–8 C atoms, or $R_1$ and $R_2$ together are alkylene having 4–8 C atoms,
to produce a compound of the formula III

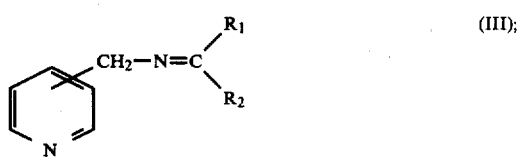

(III);

wherein $R_1$ and $R_2$ are as defined for formula II,
isomerising the compound of the formula III in the presence of a catalyst of the formula IV

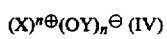 (IV)

wherein
X is an alkali metal ion or alkaline earth metal ion, or the ammonium group

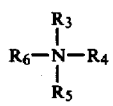

wherein $R_3$ to $R_6$ each independently of the other, are unsubstituted, straight-chain or branched-chain alkyl ($C_1$–$C_{20}$), or alkyl ($C_1$–$C_{20}$) substituted by phenyl or naphthyl, in particular, $R_3$, $R_4$ and $R_5$ are either $CH_3$ or $C_2H_5$, and $R_6$ is an alkyl group ($C_{10}$–$C_{20}$),
Y is hydrogen or alkyl having 1–12 C atoms, and
n is the charge of the alkali metal ion or alkaline-earth metal ion,
to produce a compound of the formula V

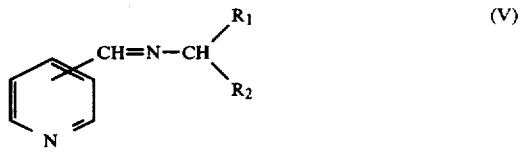

(V)

wherein $R_1$ and $R_2$ are as defined in formula II,
and converting the compound of the formula V, in the presence of an acid and optionally in the presence of a compound of the formula VI

(VI), wherein $Q_2$ is as defined for formula I, $Q_1'$ is hydrogen, alkyl having 1–4 C atoms or —SO$_3^\ominus$M$^\oplus$, $Q_3$ is hydrogen or —SO$_3^\ominus$M$^\oplus$, and M$^\oplus$ is an alkali metal cation, especially the sodium or potassium cation, into a compound of the formula I.

The above reaction can either be carried out continuously in the same reaction vessel or by a multi-stage process.

Alkyl groups $R_1$ and $R_2$ can be straight-chain or branched-chain, and preferably have 1–4 C atoms. If $R_1$ and $R_2$ are both alkyl groups, particularly alkyl groups having 1–4 C atoms, these are advantageously straight-chain. Examples of alkyl groups $R_1$ and $R_2$ as defined are: the methyl, ethyl, n-propyl, isopropyl, n-butyl, sec-butyl, tert-butyl, n-pentyl, n-hexyl, n-heptyl and n-octyl groups.

If $R_1$ and $R_2$ together form an alkylene chain, it is preferably tetramethylene and, in particular, pentamethylene.

There is preferably used in the process according to the invention a compound of the formula II wherein $R_1$ and $R_2$ are each ethyl, or together are pentamethylene, or wherein $R_1$ is hydrogen and $R_2$ is isopropyl.

The aminomethylpyridine used is preferably 3-aminomethylpyridine, and in particular 4-aminomethylpyridine.

Alkyl groups Y can likewise be straight-chain or branched-chain, and preferably have 1–6, and in particular 1–4, C atoms. Y particularly preferably is tert-butyl. X is for example lithium, potassium, sodium, magnesium, calcium or barium. Preferably X is an alkali metal, especially sodium or potassium. Particularly preferred compounds of the formula IV are sodium methylate or potassium methylate, sodium ethylate or potassium ethylate, sodium isopropylate or potassium isopropylate and, in particular, sodium tert-butylate or potassium tert-butylate. Alkyl groups $Q_1$ and alkyl or alkoxy substituents on phenyl groups $Q_2$ are advantageously straight-chain, and they have especially 1 or 2 C atoms. $Q_1$ is particularly preferably hydrogen or methyl. If phenyl groups $Q_2$ are substituted by halogen atoms, they are for example bromine and above all chlorine atoms. Phenyl groups $Q_2$ can contain several identical or different substituents as defined, they preferably carry however only one of the substituents mentioned. Suitable hydrazines of the formula VI to be mentioned are for example: phenylhydrazine, α- or β-naphthylhydrazine, phenyl-N-methylhydrazine, N-phenyl-N-ethylhydrazine, N-4-methyl-, N-4-ethyl-, N-4-methoxy-, N-4-ethoxy- and N-4-chlorophenylhydrazine or -N-methylhydrazine, and the corresponding sulfonic acid salts. Particularly preferred as compounds of the formula VI are N-phenyl-N-methylhydrazine, the sodium salt of 1-(4′-methoxyphenyl)-2-sulfohydrazine or of 1-(4′-methoxyphenyl)-1,2-disulfohydrazine, and especially phenylhydrazine.

The aminomethylpyridines and also the compounds of the formulae IV and VI are known per se.

The reaction of the aminomethylpyridine with a compound (aldehyde or ketone) of the formula II and the isomerisation of a compound of the formula III to a compound of the formula V are advantageously performed in the presence of an inert organic solvent. The inert organic solvents used are advantageously aprotic organic solvents, particularly aliphatic or aromatic hydrocarbons, aliphatic or cyclic ethers, ethylene glycol- and diethylene glycol-dialkyl ethers, dialkylsulfoxides having 1–4 C atoms in each of the alkyl moieties, or N,N-dialkylamides of aliphatic monocarboxylic acids having 1–3 C atoms in the acid moiety, and alcohols. Examples of solvents of this kind are: n-pentane, n-hexane, n-heptane, benzene, toluene, xylenes, diethyl ether, di-n-propyl ether, tetrahydrofuran, tetrahydropyrane, dioxane, ethylene glycol- and diethylene glycol-dimethyl ether and -diethyl ether, dimethylsulfoxide, N,N-dimethylformamide, methanol, ethanol, n- and iso-propanol, n-butanol, tert-butanol or n-hexanol. It is also possible to use mixtures of such solvents. Preferred solvents are benzene, dioxane, tetrahydrofuran, diethyl ether and particularly toluene.

The reaction temperatures in the case of isomerisation, that is, the conversion of the compound III into the compound V, are in the process according to the invention advantageously between 0° and 80° C., and in particular between about 10° and 60° C.

The aminomethylpyridine and the compound of the formula II are used in at least a stoichiometric amount. It is advantageous to use a slight excess of the compound of the formula II, for example an approximately 5–20% excess.

The catalysts of the formula IV are advantageously used in an amount of at least 0.1 mol %, relative to the compound of the formula III. Amounts of about 0.5 to 15 mol %, relative to the compound of the formula III, are preferred. The conversion of compounds of the formula V into compounds of the formula I wherein Z is —CHO is performed preferably in a strongly acid aqueous medium. The acid used is advantageously an inorganic acid, such as hydrochloric acid or sulfuric acid. The acid is used in general in at least a stoichiometric amount, relative to the compound of the formula V, and preferably in excess. Pyridinaldehydes of the formula I which are obtained according to the invention can optionally be converted, also in a manner known per se, by reaction with hydrazines of the formula VI into the corresponding hydrazones of the formula I (see for example German Pat. No. 1,133,054), or also into other derivatives, such as aldoximes, semicarbazones or thio-semicarbazones. Hydrazones of the formula I as defined can however be produced by the process according to the invention also without intermediate isolation of the pyridinaldehydes, under mild reaction conditions, directly from the compounds of the formula V. This is of particular advantage with regard to the oxidation sensitivity of the pyridinaldehydes and/or to the further utilisation of the compounds of the formula I wherein Z≠—CHO, for example for producing cationic dyes.

The direct reaction of compounds of the formula V with the hydrazines of the formula VI to compounds of the formula I wherein Z is

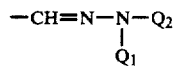

is performed, depending on the nature of the hydrazine, in an aqueous or organic medium and in the presence of an inorganic or organic acid. If $Q_3$ and/or $Q_1'$ are (or is) an —SO$_3^\ominus$M$^\oplus$—group, the reaction is preferably performed in an aqueous medium and in the presence of an inorganic acid, such as hydrochloric acid. The acid in this case is advantageously used in at least a stoichiometric amount. If $Q_3$ is hydrogen and $Q_1'$ is hydrogen or alkyl, the reaction is advantageously performed in the presence of an inert organic solvent and of an organic acid. In the latter case, only catalytic amounts of acid are in general required. The organic solvents used are advantageously inert aprotic organic solvents of the aforementioned type or mixtures thereof. There are advantageously used as organic acid aliphatic or aromatic monocarboxylic acids or monosulfonic acids, such as formic acid, acetic acid, propionic acid, butyric acid, n-valeric acid, methanesulfonic acid, benzoic acid, benzenesulfonic acid and p-toluenesulfonic acid. Anhydrous acetic acid is particularly preferred.

The amines

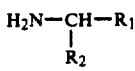

formed as by-products during the conversion into compounds of the formula I can be readily separated from the reaction medium and again utilised.

The intermediates of the formula III and/or V can optionally be isolated in a manner known per se, for example by means of distillation. An intermediate isolation of this kind is however not absolutely necessary, and a particular advantage of the process according to the invention is that the process can also be carried out continuously in the same reaction vessel without any noticeable reduction in yield of the compound of the formula I.

After completion of the reaction, the compounds of the formula I can be isolated and purified in the customary manner, for example where Z is —CHO by extraction with a suitable organic solvent. The compounds of the formula I in which Z is

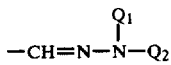

are obtained generally in crystalline form. The compounds of the formula I can be produced by the process according to the invention in very good yields (about 70–95%, especially 80%, of theory, relative to the starting aminomethylpyridine).

The preferred process variant consists in producing pyridine compounds of the formula I, wherein Z is the

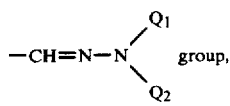

i.e. the compound VI (hydrazine is used), using aminomethylpyridine as starting material by the continuous method without isolation of the intermediates formed.

The compounds of the formula I are known and they constitute valuable intermediates (for example 2- or in particular 4-pyridinehydrazone) for producing various derivatives, such as pharmaceutical preparations, herbicides or dyes, particularly cationic dyes (see for example U.S. Pat. Nos. 2,749,351, 3,160,633 and 3,274,206, and also German Pat. No. 1,133,054).

The following Examples illustrate the procedure for carrying out the process according to the invention. "Pa" signifies Pascal = international unit of pressure.

EXAMPLE 1

(a) Production of isobutylidene-4-aminomethylpyridine

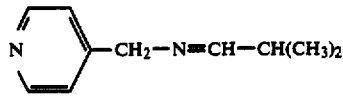

227 g (3.15 mols) of isobutyraldehyde is added dropwise, within 1.5 hours, to a solution of 324 g (3.0 mols) of 4-aminomethylpyridine in 300 ml of benzene, the addition being made in a manner ensuring that the temperature in the solution does not exceed 35° C. The water which has formed (about 39 g) is separated, and the benzene (with residual water) is distilled off under a slight water-jet vacuum. The residue is distilled in an oil-pump vacuum. After a small preliminary fraction of 5 g, there is obtained 445 g (2.75 mols) of isobutylidene-4-aminomethylpyridine as a slightly yellowish main fraction, corresponding to a yield of 91.5% of theory; b.p. 81.5°–82° C./133 Pa; $n_D° = 1.5105$.

Analysis for $C_{10}H_{14}N_2$ (molecular weight 162.24): calculated: C 74.03%; H 8.70%; N 17.27%; found: C 73.9%; H 8.8%; N 17.5%.

$^1$H-NMR spectrumτ[ppm]: 1.49(d), 2.23(d), 2.83(d), 5.48(s), 7.48(m), 8.87(d), in the ratio of 2:1:2:2:1:6.

(b) Production of 4-pyridylmethylidene-isobutylamine

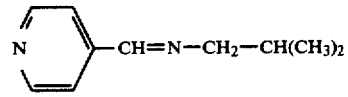

96 g (0.593 mol) of isobutylidene-4-aminomethylpyridine is added dropwise at 40° C. in the course of 30 minutes, with stirring, to a suspension of 2 g (0.0179 mol) of potassium tert-butylate in 100 ml of toluene. The reaction mixture becomes in the process darkish red-brown. It is stirred at 40° C. for a further 1.5 hours, and the toluene is distilled off in a water-jet vacuum. The residue is then distilled in an oil-pump vacuum to obtain 85 g (0.525 mol) of 4-pyridylmethylidene-isobutylamine as a slightly yellowish liquid, corresponding to a yield of 88.5% of theory; b.p. 62°–63° C./1.3 Pa; $n_D^{20} = 1.5166$.

$^1$H-NMR spectrumτ[ppm]: 1.36(d), 1.82(s), 2.45(d), 6.54(dd), 7.99(m), 9.06(d), in the ratio of 2:1:2:2:1:6.

(c) Production of 4-pyridinaldehyde-phenylhydrazone 100 g (0.617 mol) of 4-pyridylmethylidene-isobutylamine is dissolved in 100 ml of toluene; 2 g of glacial acetic acid is added to the solution, and, within 25 minutes, 67.5 g (0.649 mol) of phenylhydrazine is added dropwise, with the temperature rising to 60° C. After the addition of about 2/3 of the phenylhydrazine, the product commences to precipitate in the form of small yellow needles. The reaction mixture is stirred at room temperature (20°–25° C.) for a further hour; the product is then filtered off, washed with a small amount of cold toluene, and dried at 50° C. in a vacuum-drying chamber. The yield is 115 g (0.584 mol) of 4-pyridinaldehyde-phenylhydrazone in the form of a finely crystalline yellow product, corresponding to a yield of 94.5% of theory; m.p. 178°-180° C. (total yield 78%, relative to 4-aminomethylpyridine).

Analysis for C₁₂H₁₁N₃ (molecular weight 197.24): calculated: C 73.08%; H 5.62%; N 21.31%; found: C 73.1%; H 5.6%; N 21.4%.

(d) Conversion of 4-pyridinaldehyde-phenylhydrazone into a dye 19.7 g of 4-pyridinaldehyde-phenylhydrazone produced by the above process is suspended in 250 ml of water. After the addition of 2.0 g of magnesium oxide, 25.2 g of dimethyl sulfate is added dropwise at 25°-30° C. with stirring. Stirring is continued for 2 hours, and the dye solution obtained is filtered; the filtrate is then cooled to 0° C., and 10.0 g of dimethyl sulfate and subsequently 40 ml of 30% sodium hydroxide solution are added. The reaction mixture is stirred for 1 hour, with the internal temperature being kept below 20° C. by the addition of ice. The pH value is then adjusted to 4-5 by means of concentrated hydrochloric acid, and the dye of the formula

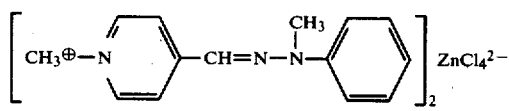

is precipitated by the dropwise addition of 13.0 ml of 50% zinc chloride solution.

EXAMPLE 2

75 g (1.04 mols) of isobutyraldehyde is added dropwise within one hour to a solution of 102 g (0.945 mol) of 4-aminomethylpyridine in 350 ml of toluene. After the dropwise addition is completed, the cloudy emulsion formed is stirred for a further hour at room temperature, and the water which has formed is separated. The unreacted aldehyde and the residual water are subsequently distilled off azeotropically in a water-jet vacuum, with about half the employed toluene concomitantly distilling over. To the toluene solution is then added 5 g (0.045 mol) of potassium tert-butylate, whereupon the reaction mixture assumes a dark-violet shade, and is stirred at 35° C. for 1.5 hours. It is acidified with 5 g of glacial acetic acid, and 107 g (1.03 mols) of phenylhydrazine is added dropwise within 15 minutes, in the course of which phenylhydrazone precipitates in the form of small yellow needles. The result is 142.5 g (0.723 mol) of 4-pyridinaldehyde-phenylhydrazone, corresponding to a yield of 76.5% of theory, relative to the 4-aminomethylpyridine used; m.p. 177°-179° C.

EXAMPLE 3

If there is used in Example 1(b), with otherwise the same procedure, 100 ml of dioxane in place of 100 ml of toluene, there is obtained, after further reaction and processing in the manner described in Example 1(c), 4-pyridinaldehyde-phenylhydrazone in a yield of 69.5% of theory, relative to the 4-aminomethylpyridine used.

EXAMPLE 4

By using in Example 1(b), instead of 100 ml of toluene, the same amount of tetrahydrofuran, with lowering of the reaction temperature to 0° C., there is obtained, by further reaction and processing in the manner described in Example 1(c), 4-pyridinaldehyde-phenylhydrazone in a yield of 70.5% of theory, relative to the 4-aminomethylpyridine used.

EXAMPLE 5

By using instead of 100 ml of toluene in Example 1(b) the same amount of diethyl ether, there is obtained, by further reaction and processing in the manner described in Example 1(c), 4-pyridinaldehyde-phenylhydrazone in a yield of 68% of theory, relative to the 4-aminomethylpyridine used.

EXAMPLE 6

(a) Production of isobutylidene-3-aminomethylpyridine

The procedure as in Example 1(a) is carried out except that 54.07 g (0.5 mol) of 3-aminomethylpyridine, 40 g (0.55 mol) of isobutyraldehyde and 75 ml of toluene are used. Distillation yields 80.1 g (0.495 mol) of isobutylidene-3-aminomethylpyridine; yield 98.8% of theory; b.p 106°-108° C./1.8×10³ Pa; $n_D^{20}=1.5103$.

Analysis for C₁₀H₁₄N₂ (molecular weight 162.24): calculated: C 74.03%; H 8.70%; N 17.27%; found: C 73.44%; H 8.74%; N 16.90%.

MS spectrum: molecular peak 162, masses of the fragments 147, 133, 119, 92, 65.

¹H-NMR spectrumτ[ppm]: 1.5(m), 2.2-2.5(m), 2.78(dd), 5.44(s), 7.5(m), 8.84(d) in the ratio of 2:2:1:2:1:6.

(b) Production of 3-pyridylmethylidene-isobutylamine

The procedure is carried out as in Example 1(b) but with the use of 80.1 g (0.495 mol) of isobutylidene-3-aminomethylpyridine, 2.5 g (0.0223 mol) of potassium tert-butylate and 75 ml of toluene. After a reaction time of 1 hour at 30°-35° C., distillation yields 74.5 g (0.46 mol) of 3-pyridylmethylidene-isobutylamine; yield 93% of theory; b.p. 108° C./2×10³ Pa; $n_D^{20}=1.5198$.

Analysis for C₁₀H₁₄N₂ (molecular weight 162.24): calculated: C 74.03%; H 8.70%; N 17.27%; found: C 73.84%; H 8.78%; N 17.18%. MS spectrum: molecular peak 162, masses of the fragments 147, 119, 105, 92. ¹H-NMR spectrum τ [ppm]: 1.12(d), 1.36(dd), 1.72(s), 1.88(dt), 2.69(dd), 6.54(dd), 7.97(m), 8.98(d) in the ratio of 1:1:1:1:2:1:6.

(c) Production of 3-pyridinaldehyde 81 g (0.5 mol) of 3-pyridylmethylidene-isobutylamine is added dropwise to a solution of 100 ml of 37% hydrochloric acid and 100 ml of water. The solution is then adjusted to pH 3 with sodium hydroxide solution; it is subsequently saturated with sodium nitrate, and extracted with three 150 ml portions of chloroform. After drying of the chloroform phase with anhydrous sodium sulfate, the solvent is distilled off to leave 47.5 g (0.44 mol) of 3-pyridinaldehyde; yield 88% of theory; b.p. 80°-82° C./1.7×10³ Pa; $n_D^{20}=1.5488$.

The pyridinaldehyde obtained can be converted in a manner known per se, by reaction with suitable hydrazines and subsequent quaternisation of the resulting pyridine hydrazone, into cationic dyes which produce on polyacrylonitrile fibres dyeings having very good fastness properties.

EXAMPLE 7

The procedure is carried out as described in Example 2 but with the use of 54 g (0.5 mol) of 3-aminomethylpyridine, 120 ml of toluene, 40 g (0.55 mol) of isobutyraldehyde, 2.5 g (2.5 g (0.0225 mol) of potassium tertbutylate and 54 g (0.5 mol) of phenylhydrazine. There is obtained after processing 78.6 g (0.4 mol) of 3-pyridinaldehyde-phenylhydrazone, corresponding to a yield of 80% of theory, relative to the 3-aminomethylpyridine used; m.p. 156°–157° C.

Analysis for $C_{12}H_{11}N_3$ (molecular weight 197.24): calculated: C 73.08%; H 5.62%; N 21.31% found: C 72.65%; H 5.59%; N 21.32%.

MS spectrum: molecular peak 197, masses of the fragments 169, 92, 65.

EXAMPLE 8

(a) Production of 1-ethylpropylidene-3-aminomethylpyridine

The procedure is carried out in the manner described in Example 1(a) except that 54.1 g (0.5 mol) of 3-aminomethylpyridine, 45.2 g (0.525 mol) of diethyl ketone and 80 ml of benzene are used. After a reaction time of 4 hours at reflux temperature on a water separator and subsequent distillation, there is obtained 83 g (0.472 mol) of 1-ethylpyropylidene-3-aminomethylpyridine; yield 94.2% of theory; b.p. 75° C./4 Pa.

Analysis for $C_{11}H_{16}N_2$ (molecular weight 176.26): calculated: C 74.96%; H 9.15%; N 15.89%; found: C 74.80%; H 9.30%; N 15.80%.

MS spectrum: molecular peak 176, masses of the fragments 147, 92, 65.

$^1$H-NMR spectrum $\tau$ [ppm]: 1.5(m), 2.3(m), 2.8(dd), 5.48(s), 7.65(m), 8.87(m) in the ratio of 2:1:1:2:4:6.

(b) Production of 3-pyridinaldehyde-phenylhydrazone 80.39 g (0.45 mol) of 1-ethylpropylidene-3-aminomethylpyridine is added to a suspension of 2 g (0.0179 mol) of potassium tert-butylate in 80 ml of toluene and 10 ml of dimethyl sulfoxide, with the temperature rising immediately from 22° C. to 26° C. After a reaction time of 5 hours at 35° C., there are added within 10 minutes 50 g (0.48 mol) of phenylhydrazone and 1 g of glacial acetic acid. The result is 68.5 g (0.348 mol) of 3-pyridinaldehyde-phenylhydrazone; yield 77.2% of theory; m.p. 156° C.

EXAMPLE 9

(a) Production of cyclohexylidene-3-aminomethylpyridine

The procedure is carried out as described in Example 8(a) but with the use of 54.1 g (0.5 mol) of 3-aminomethylpyridine and 55 g (0.561 mol) of cyclohexanone. There is obtained after distillation 89.5 g (0.476 mol) of cyclohexylidene-3-aminomethylpyridine; yield 95% of theory; b.p. 107° C./4 Pa.

Analysis for $C_{12}H_{16}N_2$ (molecular weight 188.27): calculated: C 76.56%; H 8.57%; N 14.88%; found: C 75.79%; H 8.72%; N 14.63%.

MS spectrum: molecular peak 188, masses of the fragments 173, 159, 145, 92, 80, 65.

$^1$H-NMR spectrum $\tau$ [ppm]: 1.5(m), 2.35(m), 2.8(m), 5.49(s), 7.6(m), 8.3(m) in the ratio of 2:1:1:2:4:6.

(b) Production of 3-pyridinaldehyde-phenylhydrazone

The procedure is carried out as described in Example 8(b) but with the use of 87.2 g (0.464 mol) of cyclohexylidene-3-aminomethylpyridine in place of 80.39 g (0.45 mol) of 1-ethylpropylidene-3-aminomethylpyridine. There is obtained 66.5 g (0.388 mol) of 3-pyridinaldehydephenylhydrazone; yield 72.8% of theory; m.p. 156°–157° C.

EXAMPLE 10

(a) Production of isobutylidene-2-aminomethylpyridine

The procedure is carried out as described in Example 1(a) but with the use of 216 g (2 mols) of 2-aminomethylpyridine and 144 g (2 mols) isobutyraldehyde. After a reaction time of 2 hours at 35°–40° C., subsequent distillation leaves 277 g (1.71 mols) of isobutylidene-2-aminomethylpyridine; yield 85.5% of theory; b.p. 69° C./200 Pa.

Analysis for $C_{10}H_{14}N_2$ (molecular weight 162.24): calculated: C 74.03%; H 8.70%; N 17.27%; found: C 73.74%; H 8.72%; N 16.88%.

$^1$H-NMR spectrum $\tau$ [ppm]: 1.44(d), 2.2–2.45(m), 2.6–2.95(m), 5.29(s), 7.45(m), 8.83(d) in the ratio of 1:2:2:2:1:6.

(b) Production of 2-pyridylmethylidene-isobutylamine

The procedure is carried out as described in Example 1(b) but with the use of 138 g (0.85 mol) of isobutylidene-2-aminomethylpyridine, 150 ml of toluene and 4 g (0.036 mol) of potassium tert-butylate. After a reaction time of 30 minutes at 40° C. and subsequent distillation, there is obtained 92 g (0.57 mol) of 2-pyridylmethylidene-isobutylamine; yield 67% of theory; b.p. 95° C./2.0×10$^3$ Pa.

Analysis for $C_{10}H_{14}N_2$ (molecular weight 162.24): calculated: C 74.03%; H 8.70%; N 17.27%; found: C 74.11%; H 8.69%; N 17.14%.

MS spectrum: molecular peak 162, masses of the fragments 147, 119, 92, 65.

$^1$H-NMR spectrum $\tau$ [ppm]: 1.35(d), 1.62(s), 1.97(d), 2.28(dt), 2.7(m), 6.48(dd), 7.92(sep), 8.96(d) in the ratio of 1:1:1:1:1:2:1:6.

(c) Production of 2-pyridinaldehyde-phenylhydrazone

The procedure is carried out as described in Example 1(c) but with the use of 100 g (0.617 mol) of 2-pyridylmethylideneisobutylamine. After the addition of 67.5 g (0.649 mol) of phenylhydrazone, there is obtained 116.5 g (0.592 mol) of 2-pyridinaldehyde-phenylhydrazone, corresponding to a yield of 95.9% of theory; m.p. 179° C.

Analysis for $C_{12}H_{11}N_2$ (molecular weight 197.24): calculated: C 73.08%; H 5.62%; N 21.31%; found: C 73.2%; H 5.6%; N 21.4%.

EXAMPLE 11

The procedure is carried out as described in Example 1(b) but with the use of 35 ml (0.0175 mol) of a 0.5-molar toluene solution of trimethylalkylammonium hydroxide [N(CH$_3$)$_3$R]OH(R=C$_8$–C$_{18}$, mean molecular weight = 266.05) instead of 2 g (0.0179 mol) of potassium tert-butylate. After a reaction time of 15 hours at 40° C., there is obtained 4-pyridylmethylidene-isobutylamine in a yield of 40% of theory.

EXAMPLE 12

The procedure is carried out as described in Example 2 but with the use of a solution of 1.3 g (0.0116 mol) of potassium tert-butylate in 8 ml of tert-butanol instead of 5 g (0.045 mol) of potassium tert-butylate. After a reaction time of 5 hours at 45° C., there is obtained 4-pyridinaldehyde-phenylhydrazone in a yield of 76% of theory.

EXAMPLE 13

400 ml of a solution of the sodium salt of p-methoxyphenylhydrazine-α,β-disulfonic acid (produced from 30.75 g (0.25 mol) of p-anisidine by diazotisation and sulfite reduction) is added dropwise to a mixture of 32.4 g (0.20 mol) of 4-pyridylmethylidene-isobutylamine in 35 ml of toluene and 250 ml of concentrated hydrochloric acid. The reaction mixture is stirred for 15 minutes at 30° C.; it is subsequently neutralised with sodium hydroxide solution, and the 4-pyridinaldehyde-p-methoxyphenylhydrazone which has precipitated is filtered off, washed with water and dried. Yield: 42 g, corresponding to 92%, relative to the Schiff base; m.p. 147°–152° C.

What is claimed is:

1. A process for producing a compound of the formula I

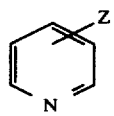  (I)

wherein
Z is

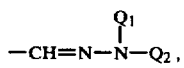

$Q_1$ is hydrogen or alkyl having 1–4 C atoms, and
$Q_2$ is phenyl which can be substituted by halogen, alkyl or alkoxy each having 1–4 C atoms, or is naphthyl,
which comprises the steps of:
reacting in an inert organic solvent an at least stoichiometric amount of an aminomethylpyridine and of a compound of the formula II

  (II)

wherein
$R_1$ is hydrogen or alkyl having 1–8 C atoms,
$R_2$ is alkyl having 1–8 C atoms, or $R_1$ or $R_2$ together are alkylene having 4–8 C atoms,
to produce a compound of the formula

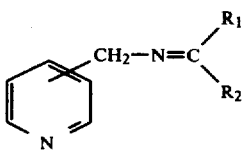  (III)

wherein $R_1$ and $R_2$ are as defined for formula II,
isomerizing said compound III in said solvent at a temperature from 0° to 80° C., in the presence of at least 0.1 mole %, relative to the amount of said compound III, of a catalyst of the formula IV

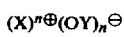  (IV)

wherein

X is an alkali metal ion or alkaline earth metal ion, or the ammonium group

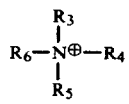

wherein $R_3$ to $R_6$ each independently of the other, are unsubstituted straight-chain or branched-chain alkyl having 1–20 C atoms or alkyl having 1–20 C atoms substituted by phenyl or naphthyl,
Y is hydrogen or alkyl having 1–12 C atoms, and
n is the charge of the alkali metal ion or alkaline-earth metal ion,
to produce a compound of formula V

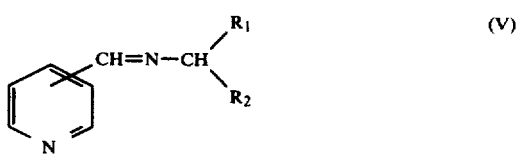  (V)

wherein $R_1$ and $R_2$ are as defined in formula II, and,
finally converting said compound V, in the presence of at least a stoichiometric amount of an inorganic acid and in an aqueous medium or in in the presence of a catalytic amount of an organic acid and in an inert organic solvent, and in the presence of a compound of the formula VI

  (VI), wherein $Q_2$ is as defined for formula I,
$Q_1'$ is hydrogen, alkyl having 1–4 C atoms or —SO$_3^\oplus$ M$^\ominus$,
$Q_3$ is hydrogen or —SO$_3^\oplus$ M$^\ominus$, and
M$^\oplus$ is an alkali metal cation,
into a compound of the formula I.

2. A process according to claim 1 for the production of compounds of the formula I using aminomethylpyridine as starting material, by carrying out the reaction steps consecutively in the same reaction vessel without isolation of the resulting intermediates.

3. A process according to claim 1, wherein isomerisation of the compound III is performed at a temperature between 10° and 60° C.

4. A process according to claim 1, wherein the starting material is 3-aminomethylpyridine or 4-aminomethylpyridine.

5. A process according to claim 1, wherein a compound of formula II is used in which $R_1$ and $R_2$ are each ethyl or together they are pentamethylene, or $R_1$ is hydrogen and $R_2$ is isopropyl.

6. A process according to claim 1, wherein a compound of formula IV is used in which X is an alkali metal ion, and Y is alkyl having 1–4 C atoms.

7. A process according to claim 1 wherein the reaction of a compound of the formula V with a compound of the formula VI, in which $Q_3$ is hydrogen and $Q_1'$ is hydrogen or alkyl having 1–4 C atoms, is performed in the presence of an inert organic solvent and of an organic acid, and the reaction with a compound of the formula VI, in which at least one of $Q_3$ and $Q_1'$ is an —SO$_3^\ominus$M$^\oplus$— group, is performed in an aqueous medium and in the presence of an inorganic acid.

8. A process according to claim 7, wherein the organic acid is an aliphatic or aromatic monocarboxylic acid or monosulfonic acid.

9. A process according to claim 7, wherein the compound of formula VI is phenylhydrazine, N-phenyl-N-methylhydrazine, the sodium salt of 1-(4'-methoxyphenyl)-2-sulfohydrazine or 1,2-disulfohydrazine.

10. A process according to claim 1, wherein a compound of formula IV is used in which X is sodium or potassium and Y is tert-butyl.

11. A process according to claim 1, wherein the compound of formula VI is used in which M$^\oplus$ is sodium or potassium.

12. A process according to claim 1, wherein the compound of formula IV is used in which X is the ammonium group

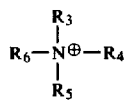

wherein R$_3$, R$_4$, R$_5$ are CH$_3$ or C$_2$H$_5$ and R$_6$ is alkyl of 10–20 C atoms.

* * * * *